United States Patent [19]

Nunogaki

[11] Patent Number: 4,813,420

[45] Date of Patent: Mar. 21, 1989

[54] HEMOLYSIS REACTION MEASURING DEVICE

[75] Inventor: Yoshiaki Nunogaki, Nagaokakyo, Japan

[73] Assignee: Sanki Engineering Ltd., Kyoto, Japan

[21] Appl. No.: 111,031

[22] Filed: Oct. 20, 1987

[30] Foreign Application Priority Data

Oct. 20, 1986 [JP] Japan .................... 61-160951[U]

[51] Int. Cl.$^4$ ............................................. G01N 33/48
[52] U.S. Cl. .................................. 128/633; 128/635;
604/65; 356/39; 356/41
[58] Field of Search ............... 356/39, 40, 41; 604/65;
128/633, 635

[56] References Cited

U.S. PATENT DOCUMENTS 3,799,672  3/1974  Vurek ........................... 128/633 X
4,357,105  11/1982  Loretz ................................ 356/40
4,444,498  4/1984  Heinemann ..................... 356/41 X
4,603,700  8/1986  Nichols et al. ....................... 28/633

*Primary Examiner*—Allen M. Ostrager
*Attorney, Agent, or Firm*—Wenderoth, Lind & Ponack

[57] ABSTRACT

A hemolysis reaction measuring device includes a hemolysis reacting member made of a light transmitting material and adapted to cause hemolysis reaction to take place therein, a light source supported so as to be able to project light toward a side portion of the hemolysis reacting member, and a light receiving member which allows the light emitted from the light source and passing through the hemolysis reacting member to be incident upon it so as to measure light absorbance of a liquid within the hemolysis reacting member based on the intensity of the incident light. The light source is formed by a light emitting diode.

1 Claim, 2 Drawing Sheets

HEMOLYSIS REACTION MEASURING DEVICE

BACKGROUND OF THE INVENTION

The present invention generally relates to a measuring apparatus, and more particularly, to a hemolysis reaction measuring device for measuring osmotic pressure resistance of erythrocytes, i.e., red blood corpuscles or red blood cells.

A known conventional hemolysis reaction measuring device is disclosed, for example, in Japanese Utility Model Publication (Jikkosho) No. 54-13832.

The known measuring device is provided with a hemolysis reacting means which comprises a transparent flexible tube wound around a similarly transparent round rod. After brine or salt water is charged into the tube to provide a concentration gradient, blood is poured thereinto from a high concentration portion. Subsequently opposite ends of the tube are closed, and by causing said tube to revolve and rotate, the red blood cells are slowly moved toward a low osmotic pressure portion. Thus, to employ a phenomenon in which the moving red blood cells are soon subject to hemolysis at a point of certain osmotic pressure to form a red hemolysis zone within the tube, a light source is provided so as to be able to project light toward a side portion of said tube, with the tube being adapted to be displaced along a center axis thereof, to thereby record the pattern of light absorbance within the tube, for example, by a scanning type photoelectric recorder.

It is to be noted here that the patterns of the hemolysis zones as referred to above are used for medical examinations of various diseases.

In the conventional hemolysis reaction measuring device as described above, a halogen lamp is employed as the light source for projecting light toward the side portion of the tube.

Accordingly, the amount of heat generation is undesirably relatively large, and a fan is required for cooling purposes, thus contributing to a relatively large and complicated structure of the measuring device.

Moreover, due to the fact that the halogen lamp contains light having various wavelengths, the measurement of the light absorbance can not be effected if the light thereof is projected as it is, and therefore, it is necessary to project light onto the tube through a filter which permits only light having a specific wavelength to pass therethrough. Such a filter undesirably contributes to the cost of the device.

Furthermore, other problems are presented in that light from the halogen lamp has a high degree of noise, with an unstable light intensity, which causes a reduction in the measuring accuracy, while the life of the halogen lamp is rather short.

SUMMARY OF THE INVENTION

Accordingly, an essential object of the present invention is to provide a hemolysis reaction measuring device in which the measuring accuracy and durability is improved without employing an expensive filter.

Another important object of the present invention is to provide a hemolysis reaction measuring device of the above-described type, which is compact, has a simple construction, functions stably with high reliability, and which can be readily manufactured at a low cost.

In accomplishing these and other objects, according to one preferred embodiment of the present invention, there is provided a hemolysis reaction measuring device which includes a hemolysis reacting means made of a light transmitting material and adapted to cause hemolysis reaction to take place therein, a light source supported so as to be able to project light toward a side portion of the hemolysis reacting means, and a light receiving means which is positioned so that the light emitted from the light source and passing through the hemolysis reacting means is incident thereupon so as to measure the light absorbance of a liquid within the hemolysis reacting means based on the intensity of the incident light, with the light source being formed by a light emitting diode means.

According to the present invention, a hemolysis reaction measuring device having greater measuring accuracy and increased durability has been advantageously provided with a simple construction.

BRIEF DESCRIPTION OF THE DRAWINGS

These and other objects and features of the present invention will become clear from the following description taken in conjunction with the preferred embodiment thereof with reference to the accompanying drawings, in which.

DETAILED DESCRIPTION OF THE PREFERRED EMBODIMENT

Figure 1:
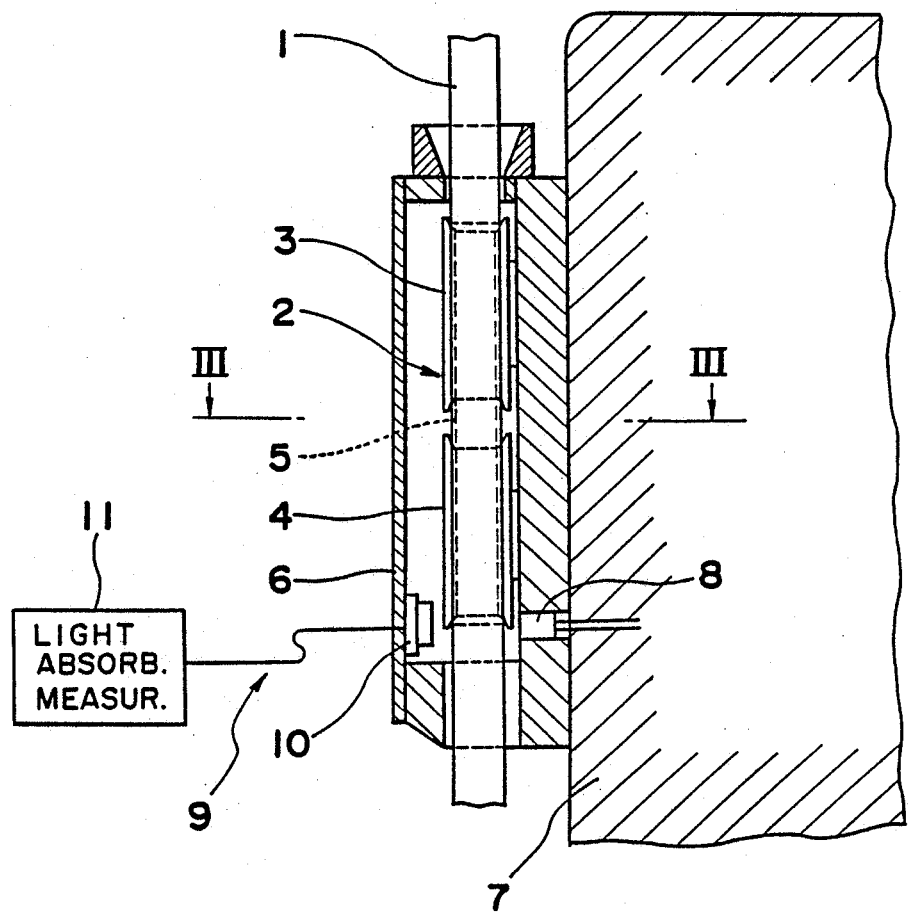
FIG. 1 is a fragmentary side sectional view of a hemolysis reaction measuring device according to one preferred embodiment of the present invention.

Before the description of the present invention proceeds, it is to be noted that like parts are designated by like reference numerals throughout the accompanying drawings.

Figure 2:
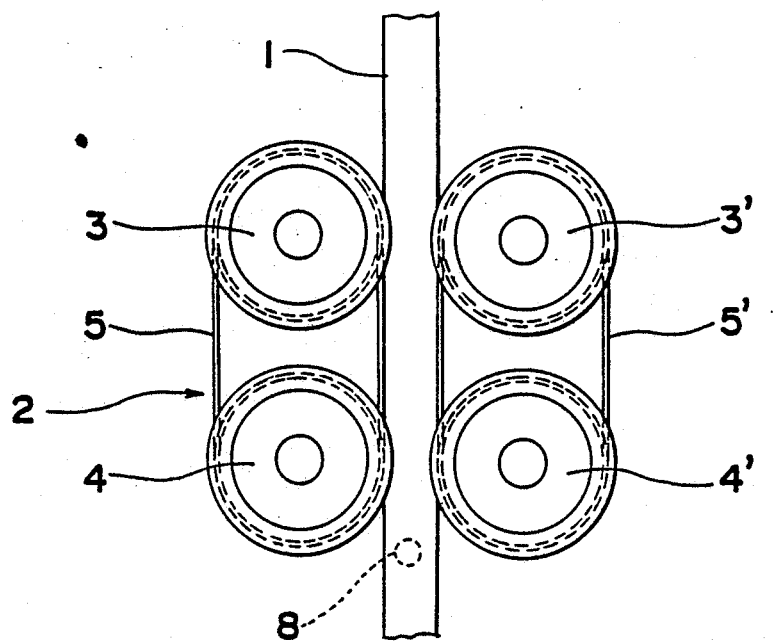
FIG. 2 is a fragmentary side elevational view showing only an elevating/lowering means portion of the measuring device of FIG. 1.
Figure 3:
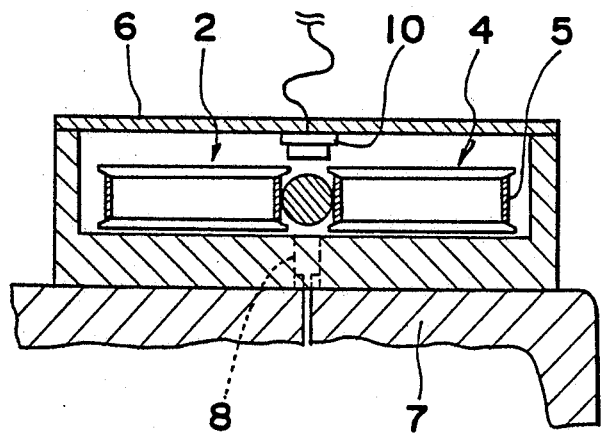
FIG. 3 is a cross-sectional view taken along the line III—III of FIG. 1.

Referring now to the drawings, there is shown in FIGS. 1 to 3, a hemolysis reaction measuring device according to one preferred embodiment of the present invention, which employs, as one example of a hemolysis reacting means, a transparent flexible tube 1 spirally wound around a transparent round rod so as to cause the hemolysis reaction to take place within said tube 1. More specifically, red blood cells are dropped into the tube 1 in which physiological salt water has been poured to provide a predetermined concentration gradient by an osmotic pressure gradient forming unit (not shown) or the like, and after being imparted with centrifugal force by a revolving/rotating device (not shown), the tube 1 is supported by an elevating/lowering means 2, and thus, the hemolysis reaction is taking place at a certain concentration of the physiological salt water.

The elevating/lowering means 2 includes a set of belt/pulley assemblies, one of the belt/pulley assemblies having a driving pulley 3, a driven pulley 4 disposed thereunder and an endless belt 5 passed around said pulleys 3 and 4, and the other of the belt/pulley assemblies having a driving pulley 3', a driven pulley 4' disposed thereunder and an endless belt 5' passed around said pulleys 3' and 4'. The tube 1 is vertically held between the belts 5 and 5' of the two sets of assemblies, which are symmetrically disposed across a predetermined gap from one another so as to be elevated or lowered at a constant speed. This elevating/lowering means 2 is covered by a light shielding cover member 6 having openings at its upper and lower portions for permitting the tube 1 to enter and exit therethrough.

Moreover, at the lower portion of the elevating/lowering means 2 within the cover member 6, a light emitting diode or LED 8 (referred to as the LED hereinafter) is provided in the vicinity of the tube 1, for example, at the side of a main body 7 of the measuring device in this embodiment, while a light receiving means 9 is also provided for measuring the light absorbance within the tube 1. More specifically, the light receiving means 9 further includes a light receiving element 10 and a light absorbance measuring means 11. The light receiving element 10 is mounted on the inner wall of the covering member 6 opposite the LED 8, with the tube 1 disposed between the LED 8 and the light receiving element 10, so that said light receiving element 10 receives the light emitted by the LED 8 and transmitted through the tube 1 so as to input a signal corresponding to the intensity of the light thus received into the light absorbance measuring means 11 where the light absorbance is measured for recording.

Thus, by elevating or lowering the tube 1 at a constant speed through the elevating/lowering means 2, with the LED 8 operating a light emitting state, the light absorbance at each position of the tube 1 may be measured and recorded by the light receiving means 9, and based on this record, it can be found at which portion of the concentration of the physiological salt water, the hemolysis reaction is taking place, thus making it possible to determine the osmotic pressure resistance of the red blood cells.

It should be noted here that, in the foregoing embodiment, although the hemolysis reacting means composed of the transparent flexible tube 1 spirally wound around the transparent round rod is shown, the hemolysis reacting means of the present invention is not limited to such a hemolysis reacting means, but may be constituted by any other material which allows the light to pass therethrough, and causes the hemolysis reaction to take place therein.

It should also be noted that, in the foregoing embodiment, although the tube 1 is adapted to be raised or lowered, with the LED 8 and light receiving element 10 being fixed, the present invention is not limited to such, but may, for example, include a device in which the LED 8 and the light receiving element 10 are raised or lowered, with the tube 1 fixed.

As is clear from the foregoing description, according to the present invention, the light source is constituted by an LED. Accordingly, the power consumption by the light source is extremely reduced, with negligibly small heat generation, and a cooling fan is unnecessary thereby contributing to the very simple construction and compact size in the vicinity of the light source of the device, and, due to the fact that the light emitted from the LED has a single wavelength, an expensive filter for selecting only a single wavelength is not required, thereby contributing to a simplification of the device and a consequent reduction in cost.

Moreover, since the light from the LED has almost no noise, with its intensity being stable for a long period of time, the measuring accuracy may be improved.

Furthermore, since the life of the LED is semipermanent, the durability of the device may be improved to a large extent.

Although the present invention has been fully described in connection with the preferred embodiments thereof with reference to the accompanying drawings, it is to be noted that various changes and modifications will become apparent to those skilled in the art. Such changes and modifications are to be understood as included within the scope of the present invention as defined by the appended claims unless they depart therefrom.

What is claimed is:

1. A hemolysis reaction measuring device for detecting a hemolysis reaction occurring in a hemolysis reacting means made of a light transmitting material and adapted to facilitate the hemolysis reaction therein, said device comprising:

a light absorption detecting system comprising a light source for emitting light and a light receiving means fixed in a position relative to said light source in the device for receiving light emitted by said light source and for detecting the intensity of the light received, said light source comprising a light emitting diode; and elevating/lowering means for supporting a hemolysis reacting means between said light source and said light receiving means whereby light emitted by said light source passes through a hemolysis reacting means supported by said elevating/lowering means to said light receiving means, and for moving said light absorption detecting system and a supported hemolysis reaction means vertically relative to one another at a constant rate, said elevating/lowering means comprising a set of belt/pulley assemblies, each of said belt/pulley assemblies including a driving pulley rotatably mounted in the device, a driven pulley rotatably mounted in the device and spaced from said driving pulley, and an endless belt extending around said driving and said driven pulleys, said belt/pulley assemblies spaced apart from one another a predetermined distance so as to define a gap therebetween in which a hemolysis reaction means is receivable so as to be supported by said elevating/lowering means.

* * * * *